(12) United States Patent
Jansen et al.

(10) Patent No.: US 8,084,651 B2
(45) Date of Patent: Dec. 27, 2011

(54) PROCESS FOR PURIFICATION OF GLYCEROL

(75) Inventors: Robert P. Jansen, Portela (PT);
Anthony Baiada, Dagenham (GB);
John Kerr, South Croydon (GB)

(73) Assignee: Tate & Lyle Ingredients Americas LLC, Decatur, IL (US)

( * ) Notice: Subject to any disclaimer, the term of this patent is extended or adjusted under 35 U.S.C. 154(b) by 423 days.

(21) Appl. No.: 12/390,608

(22) Filed: Feb. 23, 2009

(65) Prior Publication Data

US 2009/0247792 A1 Oct. 1, 2009

Related U.S. Application Data

(60) Provisional application No. 61/035,177, filed on Mar. 10, 2008.

(51) Int. Cl.
*C07C 31/22* (2006.01)

(52) U.S. Cl. .................................................. 568/869

(58) Field of Classification Search ................... 568/869
See application file for complete search history.

(56) References Cited

U.S. PATENT DOCUMENTS

| 4,164,507 A | 8/1979 | Blytas et al. ............... 260/412.5 |
| 4,560,812 A | 12/1985 | Blytas ............................ 568/869 |
| 7,056,439 B2 | 6/2006 | Baniel et al. ................... 210/634 |

FOREIGN PATENT DOCUMENTS

GB          513595       10/1939

OTHER PUBLICATIONS

University of BATH, "Power to the People Biofuels," www.bath.ac.uk/powerttp, the BA Festival of Science (Sep. 9-15, 2007).
PCT/US2009/036450 International Search Report (May 13, 2009).

*Primary Examiner* — Sikarl Witherspoon
(74) *Attorney, Agent, or Firm* — Williams, Morgan & Amerson, P.C.

(57) ABSTRACT

A process for the recovery of glycerol comprises contacting an aqueous feed composition that comprises water, glycerol, and at least one contaminant with a solvent extractant comprising at least one C5-C8 alkanol, optionally in admixture with at least one alkane, to form a first mixture, and separating the first mixture into a first solvent phase and a first aqueous phase. The first solvent phase comprises a majority (more than 50 wt %) of the solvent extractant and a majority of the glycerol that was present in the aqueous feed composition. The weight ratio in the first solvent phase of glycerol to a contaminant present is greater than the weight ratio of glycerol to the contaminant in the aqueous feed composition. The first aqueous phase comprises a majority of the water from the aqueous feed composition and at least some of the contaminant from the aqueous feed composition.

11 Claims, 1 Drawing Sheet

PROCESS FOR PURIFICATION OF GLYCEROL

This application claims priority from U.S. provisional patent application Ser. No. 61/035,177, filed on Mar. 10, 2008, which is incorporated herein by reference.

BACKGROUND OF THE INVENTION

Biodiesel is an alternative liquid fuel that can be produced by chemical modification of vegetable oils. In particular, the triglycerides in vegetable oils can be transesterified with methanol, yielding fatty acid methyl esters, which can be used as biodiesel. However, the process also produces glycerol, which is usually present in a mixture with various contaminants.

SUMMARY OF THE INVENTION

One aspect of the invention is a process for the recovery of glycerol from an aqueous feed composition. The process comprises (1) contacting an aqueous feed composition that comprises water, glycerol, and at least one contaminant with a solvent extractant comprising at least one C5-C8 alkanol to form a first mixture, and (2) separating the first mixture into a first solvent phase and a first aqueous phase. Optionally, the solvent extractant can comprise at least one alkane in addition to at least one C5-C8 alkanol. The first solvent phase comprises a majority ("majority" is used herein to mean more than 50 wt %) of the solvent extractant and a majority of the glycerol that was present in the aqueous feed composition. The weight ratio in the first solvent phase of glycerol to any one contaminant present is greater than the weight ratio of glycerol to the same contaminant in the aqueous feed composition. The first aqueous phase comprises a majority of the water from the aqueous feed composition and at least some of the contaminant from the aqueous feed composition.

In some embodiments of the invention, the process further comprises recovering glycerol by removing the first solvent phase from the first aqueous phase. Optionally, the process can further comprise contacting the removed first solvent phase with an aqueous composition (e.g., pure water) to form a second mixture, and separating the second mixture into a second solvent phase and a second aqueous phase. The second solvent phase can comprise a majority of the solvent extractant of second mixture, and the second aqueous phase can comprise glycerol and water, and the weight ratio in the second aqueous phase of the glycerol to any one contaminant present can be greater than the weight ratio of glycerol to the same contaminant in the aqueous feed composition.

Optionally, the process can further comprise recovering glycerol by removing the second aqueous phase from the second solvent phase. Another option is to recycle the recovered second solvent phase.

In some embodiments, the process also comprises treating the recovered second aqueous phase to further purify glycerol.

DESCRIPTION OF ILLUSTRATIVE EMBODIMENTS

Figure 1:
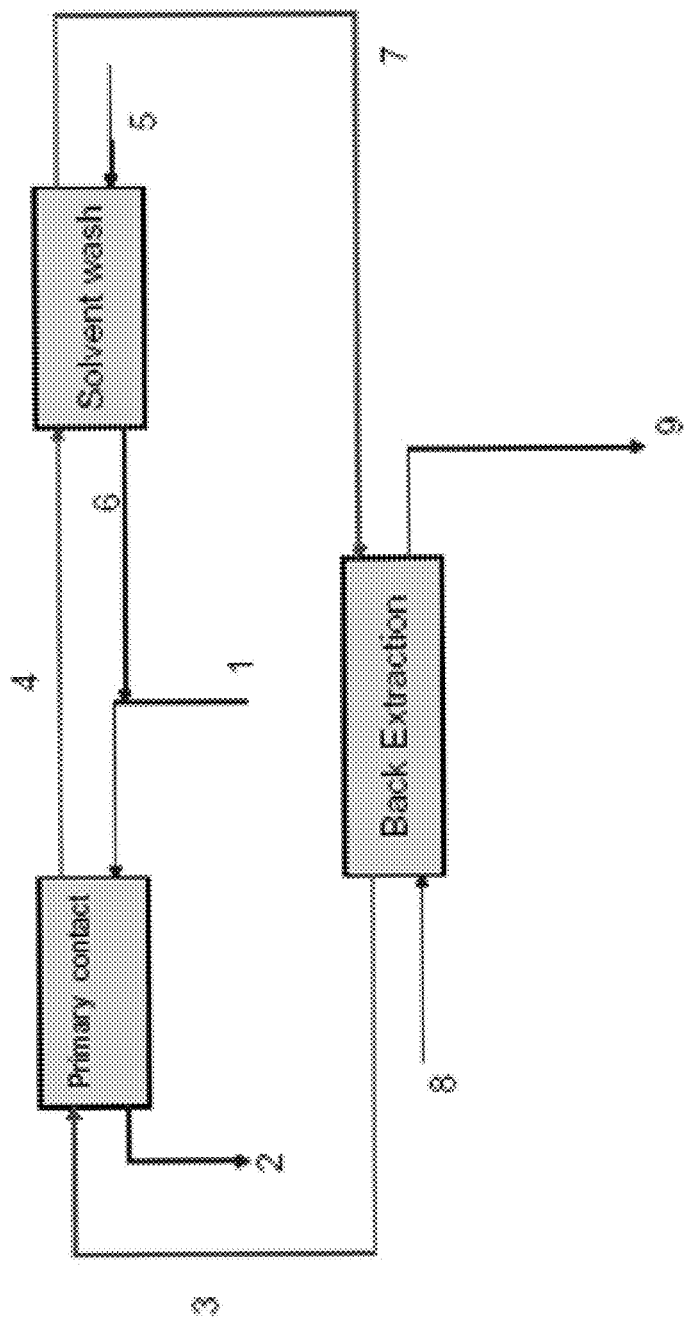
FIG. 1 is a process flow diagram in accordance with the present invention for purification of glycerol.

The process of the present invention can be used to obtain a purified glycerol composition from an impure feed that contains glycerol, water, and one or more contaminants. Examples of contaminants that can be found in aqueous glycerol compositions include, but are not limited to, organic acids, organic salts, inorganic salts, carbohydrates, alcohols, proteins, amino acids, and low molecular weight hydroxylated compounds. In one embodiment, the feed composition is an impure aqueous glycerol composition that is a by-product of biodiesel production.

As shown in FIG. 1, the crude aqueous glycerol feed composition 1 can be contacted with a solvent extractant 3. The solvent extractant (i) dissolves glycerol readily, (ii) has limited solubility in water and water has limited solubility in it, and (iii) has a specific gravity significantly different from that of the aqueous feed, allowing facile separation of the solvent phase from the aqueous phase. The solvent extractant can comprise (or in some embodiments, can consist essentially of) at least one C5-C8 alkanol. Hexanol is one example of a suitable C5-C8 alkanol.

In some embodiments, the solvent extractant can further comprise at least one alkane in addition to alkanol. For example, the solvent can contain predominantly (at least 50% by weight) an alkanol, but it can also contain an alkane (such as hexane or kerosene). The phase separation between the solvent (light) phase and the aqueous (heavy) phase can be enhanced if an alkane is added to the solvent phase.

It has surprisingly been found that the use of a solvent extractant that comprises hexanol results in a higher purity of glycerol in the product, as compared to the results obtained by using many other solvent extractants. In one embodiment of the process, the solvent extractant consists essentially of hexanol.

As a result of the contact, some mixing of the crude glycerol feed 1 and the solvent extractant 3 will occur, thereby producing a first mixture. The majority of the glycerol can be extracted into a first solvent phase 4, leaving at least some of the impurities in a first aqueous phase 2. In some embodiments, 80-90 wt % or more of the glycerol from the feed can be extracted into the first solvent phase. In some embodiments, the first aqueous phase contains the majority of the water and contaminants from the feed, and in some cases, may contain a much higher percentage (i.e., considerably more than 50%) of both.

Optionally, the contacting between solvent extractant and the aqueous phase(s) can be performed two or more times to increase the recovery of glycerol.

The first solvent phase 4 can be separated from the first aqueous phase 2. The separation can be performed using methods known in the art, such as centrifugation or decantation. In certain embodiments, the contacting step and separation of the phases can be carried out in a mixer-settler apparatus.

The first aqueous phase 2 can comprise the majority of many if not all of the contaminants that were present in the feed. Thus, the aqueous phase 2 is the primary waste stream and can be disposed of accordingly.

Optionally, the first solvent phase 4 can then be washed by contacting it with a relatively small amount of water or aqueous composition 5. In some embodiments of the invention, the ratio of water to solvent can be in the range 0.1 to 0.8. In some embodiments, the pH of the water 5 can be adjusted to 8-11 pH, so that anionic impurities are preferentially extracted into the high pH aqueous wash phase. The aqueous phase 6 from this washing step can then be pH adjusted to a level similar to the feed 1, and can be combined with the feed and sent to the primary extraction (primary contact).

The washed first solvent phase 7, which contains the majority of the glycerol from the feed, can then be contacted with a higher ratio of an aqueous solution 8, such as clean water. In one embodiment, the volume ratio of water to the solvent phase is between about 20:1 and 1:20, in some cases between about 20:1 and 1:1. Some mixing occurs between the two streams, thereby producing a second mixture, and the majority of the glycerol is back extracted into the water. The result is a glycerol-depleted second solvent phase and a glycerol-rich second aqueous phase 9. The glycerol-depleted second solvent phase can be recycled to the solvent 3 for the primary extraction stage. The glycerol-rich second aqueous phase 9 can be recovered as the product, and optionally can be subjected to further purification. The glycerol in the aqueous product composition is purer (i.e., the weight ratio of glycerol to contaminant(s) is higher) than in the aqueous feed stream.

The process can be performed in batch, semi-batch, or continuous mode. In one embodiment, the primary extraction, washing, and back extraction steps can be carried out continuously, which can allow maximum recovery of purified glycerol with minimum loss of solvent.

Optionally, the glycerol-rich second aqueous phase can be evaporated up to any desired concentration, for example a concentration needed for the feed to a fermenter. As another option, the glycerol product composition can be passed through a resin bed (e.g., weak base anion resin, weak acid cation resin, mixed bed, etc.) to remove residual anionic and cationic impurities. As another option, the purified stream can be decolorized by passage through a granulated or powdered activated carbon column. Carbon is an effective desolventizer for any residual races of solvent.

In some embodiments, the extraction, purification, and wash stages can be carried out at ambient temperature. In other embodiments, the water wash stage can be completed at higher temperatures (e.g., 50-90° C.).

The purified glycerol produced by the present invention can be used, for example, as a feedstock for fermentation (e.g., a fermentation to make citric acid). The purified glycerol can be a less expensive feed than the mono- and disaccharides that are often used in the feed for such fermentations.

Certain embodiments of the invention can be further understood from the following examples.

EXAMPLES

Comparative Example 1

Tri-butyl Phosphate 24.3 g of impure glycerol solution (containing 43% glycerol, 47% water, and ash and other impurities—see Table 1 below) were mixed with 156.68 g of "wet" TBP (TBP saturated with water contains 6% water). On standing, two phases separated. The upper phase weighed 155.51 g and the lower phase ("aqueous bottom") 24.98 g. The top phase (TBP solvent phase) was mixed with 155.51 g of water in order to transfer the glycerol back to the aqueous phase. On separation, 154.24 g of upper phase was formed and 153.53 g of lower phase. To remove any residual TBP from the lower phase, it was mixed with 29.24 g of hexane. The mixture was allowed to separate to give an upper hexane/TBP phase (28 g) and a lower aqueous phase (152.32 g; "aqueous product stream"). The purity of the glycerol in this lower phase was 19% (where % glycerol purity is defined as the wt% of glycerol per unit weight of product excluding water). Overall glycerol recovery was 98% in this experiment.

Example 2

Hexanol 24.3 g of impure glycerol solution (containing 43% glycerol, 47% water, and ash and other impurities—see Table 1 below) were mixed with 154 g of hexanol. On standing, two phases separated. The upper phase weighed 163.6 g and the lower phase ("aqueous bottom") 14.9 g. The top phase (hexanol solvent phase) was mixed with 163.62 g of water in order to transfer the glycerol back to the aqueous phase. On separation, 160.67 g of upper phase was formed and 142.66 g of lower phase. The purity of the glycerol in this lower phase ("aqueous product") was 100% +/−10% (within the analytical error—where % glycerol purity is defined as the wt% of glycerol per unit weight of product excluding water). Overall glycerol recovery was 95% in this experiment.

Table 1 below summarizes the concentrations of water, glycerol, and various ions in the feed, the aqueous bottoms, and the aqueous products.

TABLE 1

| Sample | HPLC | | Cations (ppm on sample) | | | | | | | | | | |
|---|---|---|---|---|---|---|---|---|---|---|---|---|---|
| | % H2O | Glycerol | Ca | Cu | Fe | K | Mg | Mn | Na | P | S | Sn |
| Feed | 46.5% | 42.6% | 12 | 1.03 | 82 | 159 | 4.8 | 0.417 | 12100 | 309 | 31 | 11 |
| Example 1 - aqueous bottom | 54.4% | 32.8% | 14 | 0.726 | 67 | 148 | 4.19 | 0.343 | 11300 | 1550 | 23 | 12 |
| Example 1 - aqueous product | 93.4% | 1.3% | 0.614 | 0.244 | 0.346 | 4.53 | 0 | 0.011 | 40 | 70 | 0 | 4.84 |
| Example 2 - aqueous bottom | 42.2% | 45.7% | 17 | 1.24 | 115 | 270 | 6.21 | 0.617 | 18900 | 700 | 43 | 11 |
| Example 2 - aqueous product | 98.0% | 2.2% | 0.306 | 0.107 | 3.94 | 5.92 | 0 | 0.002 | 108 | 31 | 0 | 4.39 |

| Sample | % H2O | HPLC Glycerol | Anions (ppm on sample) | | | | | | | | | | |
|---|---|---|---|---|---|---|---|---|---|---|---|---|---|
| | | | Chloride | Sulphate | Phosphate | Oxalate | Citrate | Aconitate | Lactate | Acetate | Malate | Formate | Nitrate |
| Feed | 46.5% | 42.6% | 20491 | 1238 | 119 | 94 | 0 | 0 | 377 | 0 | 99 | 252 | 135 |
| Example 1 - aqueous bottom | 54.4% | 32.8% | 20257 | 1268 | 176 | 96 | 0 | 0 | 78 | 0 | 55 | 60 | 127 |

TABLE 1-continued

| | | | | | | | | | | | | |
|---|---|---|---|---|---|---|---|---|---|---|---|---|
| Example 1 - aqueous product | 93.4% | 1.3% | 18 | 177 | 3.5 | 6.9 | 0 | 0 | 14 | 0 | 3.6 | 6.9 | 5.6 |
| Example 2 - aqueous bottom | 42.2% | 45.7% | 32172 | 1313 | 216 | 118 | 0 | 0 | 550 | 0 | 163 | 402 | 202 |
| Example 2 - aqueous product | 98.0% | 2.2% | 134 | 169 | 3.5 | 11 | 0 | 0 | 6.1 | 0 | 1.9 | 2.5 | 1.9 |

These experiments shows that it is possible to obtain a surprisingly higher purity of glycerol using hexanol as the solvent than when TBP is used as the solvent. The recovery of glycerol in the two experiments was similar.

This patent application is not intended to be an exhaustive list of all possible embodiments of the invention. Persons skilled in this field will recognize that modifications can be made to the specific embodiments that are described herein that would be within the scope of the following claims.

What is claimed is:

1. A process for the recovery of glycerol from an aqueous feed composition, comprising:
    contacting an aqueous feed composition that comprises water, glycerol, and at least one contaminant with a solvent extractant comprising at least one C5-C8 alkanol to form a first mixture; and
    separating the first mixture into a first solvent phase and a first aqueous phase;
    wherein the first solvent phase comprises a majority of the solvent extractant and a majority of the glycerol that was present in the aqueous feed composition, and the weight ratio in the first solvent phase of glycerol to any one contaminant present is greater than the weight ratio of glycerol to the same contaminant in the aqueous feed composition; and
    wherein the first aqueous phase comprises a majority of the water from the aqueous feed composition and at least some of the contaminant from the aqueous feed composition.

2. The process of claim 1, further comprising recovering glycerol by removing the first solvent phase from the first aqueous phase.

3. The process of claim 2, further comprising:
    contacting the removed first solvent phase with an aqueous composition to form a second mixture; and
    separating the second mixture into a second solvent phase and a second aqueous phase;
    wherein the second solvent phase comprises a majority of the solvent extractant of second mixture; and
    wherein the second aqueous phase comprises glycerol and water, and the weight ratio in the second aqueous phase of the glycerol to any one contaminant present is greater than the weight ratio of glycerol to the same contaminant in the aqueous feed composition.

4. The process of claim 3, further comprising recovering glycerol by removing the second aqueous phase from the second solvent phase.

5. The process of claim 4, further comprising recycling the recovered second solvent phase.

6. The process of claim 4, further comprising treating the recovered second aqueous phase to further purify glycerol.

7. The process of claim 1, wherein the contaminant is a compound selected from the group consisting of organic acids, organic salts, inorganic salts, carbohydrates, alcohols, proteins, amino acids, and low molecular weight hydroxylated compounds, and mixtures thereof.

8. The process of claim 1, wherein the solvent extractant consists essentially of hexanol.

9. The process of claim 1, wherein the solvent extractant further comprises at least one alkane.

10. The process of claim 9, wherein the solvent extractant comprises hexanol and hexane.

11. The process of claim 1, wherein the contacting of the aqueous composition with solvent extractant is done two or more times.

* * * * *